United States Patent
Mannick et al.

(10) Patent No.: US 7,419,834 B2
(45) Date of Patent: Sep. 2, 2008

(54) SYSTEM FOR DETECTION OF NITROSYLATED PROTEINS

(75) Inventors: Joan Mannick, Weston, MA (US); Benjamin Gaston, Charlottesville, VA (US); Barbara Leinweber, Eugene, OR (US)

(73) Assignees: University of Massachusetts, Boston, MA (US); University of Virginia Patent Foundation, Charlottesville, VA (US)

( * ) Notice: Subject to any disclaimer, the term of this patent is extended or adjusted under 35 U.S.C. 154(b) by 567 days.

(21) Appl. No.: 10/319,457

(22) Filed: Dec. 12, 2002

(65) Prior Publication Data

US 2004/0203068 A1 Oct. 14, 2004

Related U.S. Application Data

(60) Provisional application No. 60/339,268, filed on Dec. 12, 2001.

(51) Int. Cl.
*G01N 33/00* (2006.01)
*G01N 21/76* (2006.01)

(52) U.S. Cl. .......................... 436/116; 436/63; 436/86; 436/164; 436/172; 436/106; 422/61; 422/82.05; 422/82.08

(58) Field of Classification Search .................. 436/86, 436/63, 89, 164, 166, 172, 106, 116, 117, 436/118; 422/61, 82.05, 82.08; 435/7.1
See application file for complete search history.

(56) References Cited

U.S. PATENT DOCUMENTS 5,459,076 A 10/1995 Stamler et al.
5,891,735 A 4/1999 Stamler et al.

OTHER PUBLICATIONS

Kojima et al. "Detection and Imaging of Nitric Oxide with Novel Fluorescent Indicators: Diaminofluoresceins" Analytical Chemistry, vol. 70, No. 13, Jul. 1, 1998.*
Beckman et al., "Methods in Nitric Oxide Research," Feelisch and Stainler, Wiley, Chichester, U.K. (1996).
Fang et al., "Reductive Assays for S-nitrosothiols: Implications for measurements in biological systems," Bioche. Biophys. Res. Commun. 252:535-40 (1998).
Mannick et al., "Fas-induced capsase denitrosylation," Science 284:65 (1999).
Wang et al., "Inhibition of papain by S-nitrosothiols. Formation of mixed disulfides," J. Biol. Chem. 275(27):20467-73 (2000).
Itoh et al., "Determination and Bioimaging Method for Nitric Oxide in Biological Specimens by Diaminofluorescein Fluorometry," Analytical Biochemistry, 287:203-209 (2000).
King et al., "Assessment of S-nitrosothiols on diaminofluorescein gels." Analytical Biochemistry, 346:69-76 (2005).
Kojima et al., "Visualization of oxygen-concentration-dependent production of nitric oxide in rat hippocampal slices during aglycemia," Journal of Neurochemistry, 76:1404-1410 (2001).

* cited by examiner

*Primary Examiner*—Maureen M. Wallenhorst
(74) *Attorney, Agent, or Firm*—Fish & Richardson P.C.

(57) ABSTRACT

The present invention describes a novel, simplified method for detecting and monitoring whether the presence of nitrosylated proteins, such as S-nitrosoproteins, in a biological sample using fluorescence detection. The present invention further describes a method which can both quantify and identify the nature of nitrosylated proteins, which method is useful for monitoring both normal and disease states, in the development and screening of potential therapeutic drug species.

26 Claims, 1 Drawing Sheet

SYSTEM FOR DETECTION OF NITROSYLATED PROTEINS

CROSS-REFERENCE TO RELATED APPLICATIONS

This application claims the benefit of U.S. Provisional Application No. 60/339,268, filed on Dec. 12. 2001.

U.S. GOVERNMENT RIGHTS

This invention was made with United States Government support under Grant Nos. 1RO1 HL59337, HL10026 and GM57601-01, awarded by the national Institute of Health. The United States Government has certain rights in the invention.

BACKGROUND OF THE INVENTION

Nitric oxide (NO) has relatively recently been recognized as a biological messenger that reacts with a variety of sulfhydryl-containing molecules and enzymes to produce S-nitrosylated compounds. Since NO has a short half-life under physiological conditions, it generally exists in biological systems as adducts of amino acids, peptides, and proteins ("NO equivalents"). These NO equivalents are usually biologically active in that they behave as NO donors, and thereby possess unique pharmacological properties. The various targets for nitrosylation include serum albumin, tissue-type plasminogen activator, transcriptional activators, glyceraldehyde-3-phosphate dehydrogenase, human immunodeficiency virus protease, hemoglobin, and protein-phosphotyrosine phosphatase.

Nitrosylation can alter protein conformation, leading to the activation or inactivation of enzymes or receptor proteins. Like phosphorylation, the nitrosylation reaction behaves like a "chemical switch" that allows cells to transmit stimuli from the plasma membrane to the nucleus in a highly regulated manner. However, the functions and processes of nitrosylation are difficult to deconvolute, due to the high number of closely-related kinases, and due to the lack of currently available technology to easily and accurately measure the extent or presence of protein nitrosylation.

Sulfhydryl groups (—SH, also referred to as "thiol") are among the most reactive groups found in protein molecules. S-nitrosoproteins, S-nitrosothiols, and protein S-nitrosylation reactions are terms that refer to compounds with linkages through the thiol (—SH) group. These types of compounds play important roles in cell signaling processes such as neurotransmission, anion channel regulation, host defense and gene regulation. The chemical modification of the —SH group in proteins thus has important regulatory implications and can be used as a tool in the discovery of novel therapeutics.

Chemical modification of thiol groups occurs physiologically via oxidation reactions yielding either mixed disulfides or S-nitrosylated compounds. Alternatively, modification can occur through persulfide and trisulfide bond formation. The "S-nitrosylation" of proteins refers to the transfer of nitric oxide (NO) to sulfhydryl groups on proteins.

By way of example, some cysteine proteases such as caspase-3 and cathepsin K have been demonstrated to be inhibited by NO donors. (See Wang, Peng et al., *Inhibition of Papain by S-Nitrosothiols*, J. of Biol. Chem., 275, 2000 pp 20467-20473). Cysteine proteases play important roles in various biological processes. Elevated proteolytic activity of cysteine proteases is associated with many disease conditions, such as muscular dystrophy, inflammation, and rheumatoid arthritis. The active sites of cysteine proteases contain a cysteine sulfhydryl group which is highly sensitive to oxidation.

Compounds such as S-nitrosoglutathione (GSNO) are relevant biological molecules involved in nitrosylation reactions under physiological conditions. These compounds are also known to fluoresce, which would theoretically make their detection facile in samples derived from biological systems. However, identification of S-nitrosoproteins and measurement of their concentration following certain cellular events has proven to be extraordinarily cumbersome, thus extremely limiting its potential utility.

In light of the significant physiological implications of NO levels, it would be useful to have a diagnostic technique that can readily detect levels of NO or NO equivalents, such as S-nitrosothiols and other nitrosylated NO equivalents, to determine whether levels are normal for normal physiological conditions, or whether a patient has an existing or predisposition towards a pathophysiological condition. There is a particular need for procedures that are affordable and manageable, yet sensitive enough to detect levels of NO, or NO-adducts such as S-nitrosothiols. (See Beckman, J. S. et al., *Methods in Nitric Oxide Research*, Feelisch and Stainler, Wiley, Chichester, U.K., 1996; U.S. Pat. No. 5,891,735 to Stamler).

Representative of prior art approaches to monitoring of nitrosylation, U.S. Pat. No. 5,459,076 to Stamler et al. (incorporated herein by reference) describes a detection method that requires pretreatment with mercurous ion and a protein-precipitating agent. The samples are then monitored by chemiluminescence. This method involves cumbersome pretreatment procedures with a toxic mercury compound and, thus, presents considerable difficulties in application. It would be useful to have a simple procedure with minimal manipulation and without the use of additional chemicals.

The present invention is directed to a practical electrophoresis-based separation and identification system for cellular nitrosoproteins. The detection system meets a recognized need in the art for monitoring of NO in normal states and in disease states, provides a method for identifying and quantifying NO in normal and in disease states, and would facilitate the understanding of these processes for the development of better therapeutic drug species.

SUMMARY OF THE INVENTION

The present invention is directed towards a method for detecting the presence of nitrosylated species in biological samples. In a preferred embodiment, the biological samples are comprised of amino acid-based species. Preferably, the nitrosylated species are adducts between NO and amino acids, peptides, or proteins. The atoms forming the adducts with NO include carbon, nitrogen, sulfur, and oxygen. Preferably, the adduct is between NO and sulfur groups. More preferably, the adduct is a nitrosylated protein. Still more preferably, the protein is a nitrosothiol, or an "S-nitrosoprotein." Still more preferably, the nitrosylated protein is S-nitrosoalbumin.

In an embodiment of the invention, the method for detecting the presence of nitrosylated species in a biological sample comprises the steps of contacting the biological sample with developing reagents, exposing the sample to excitation radiation, and detecting the resultant emitted fluorescence.

In a preferred embodiment, the developing reagents comprise a fluorescence-developing agent and a molecular species bearing a reactive moiety capable of transnitrosylation.

Preferably, the reactive moiety is a thiol bearing group. More preferably, the molecular species capable of transnitrosylation is cysteine.

In yet another embodiment, the developing reagents comprise a saturated solution of copper (I) chloride. In still another embodiment, the fluorescent agent is 4,5-diaminofluoroscein. In a preferred embodiment, the developing reagents are added to the biological sample simultaneously. Alternatively, one or more of the developing reagents are added to the biological sample sequentially. Alternatively or additionally, the method of detecting nitrosylated species involves heating or incubating the biological sample to which the fluorescent-developing agent has been added in the presence of ascorbate and carboxyPTIO.

In another embodiment, the method for detecting nitrosylated species in a biological sample is also capable of quantifying the amount of nitrosylated species in the sample.

In the present invention, the wavelength of the excitation radiation is about 488 nm. The preferred fluorescent emission is monitored at a wavelength of about 530 nm.

In still another embodiment, the biological sample comprises a mixture of proteins derived from eukaryotic cells. Preferably, the mixture of proteins is derived from mammalian cells in the absence of metal chelators.

In another embodiment, the method comprises the additional step of transferring the nitrosylated species to a solid support material capable of binding prior to contacting the sample with the developing reagents. The preferred solid supports include nitrocellulose, polyamides, and other synthetic membranes capable of binding amino acid-based species.

The present invention further provides a method of detecting the presence of nitrosylated species in a biological sample comprising one or more amino acid-based species, which involves separating the amino acid-based species in the sample, contacting each of these species with developing reagents, exposing the species to excitation radiation, and detecting the emitted fluorescence.

The nitrosylated species in the separated sample comprise an adduct between NO and an amino acid-based species. The adduct is formed between NO and an atom on the amino acid-based species, including carbon, nitrogen, oxygen and sulfur. The preferred adduct is through a sulfur atom. More preferably, the preferred adduct is between NO and a sulfur atom on a protein. Still more preferably, the nitrosylated protein is S-nitrosoalbumin.

In a preferred embodiment, the developing reagents comprise a fluorescence-developing agent and a molecular species bearing a reactive moiety capable of transnitrosylation. Preferably, the reactive moiety on the molecular species is a thiol group. More preferably, the molecular species is cysteine.

In another embodiment, the developing reagents include a saturated solution of copper (I) chloride. More preferably, the fluorescence-developing agent includes 4,5-diaminofluoroscein (DAF-2). Preferably, the developing reagents are added to the biological sample simultaneously. Alternatively, one or more of the developing reagents are added to the biological sample sequentially.

In another embodiment, the method is capable of quantifying the amount of each separated nitrosylated species in the biological sample.

The method further comprises the additional step of incubating the biological sample and the developing reagent to elevated temperature in the presence of ascorbate and carboxyPTIO. Preferably, the sample is heated to around 37° C.

Preferably, the wavelength of the excitation radiation is about 488 nm. Also, the fluorescent emission is monitored at about 530 nm.

Preferably, the mixture of proteins that are separated prior to detection and quantification are derived from eukaryotic cells. More preferably, the mixture of proteins are derived from mammalian cells in the absence of metal chelators prior to separation and prior to detection and quantification. The separation can be achieved by commonly used methods that rely on the characteristic physical properties of the molecules, such as the charge, size, molecular weights, polarity, etc. Preferred methods of separation include isoelectric focusing, agarose gel electrophoresis, polyacrylamide gel electrophoresis, HPLC, and preparative chromatography. Most preferred is the method of separation using gel electrophoresis.

The invention provides the additional step of determining the chemical identity of the individual nitrosylated species in the biological sample.

Another aspect of the invention is the capability of providing a kit for detecting nitrosylated species comprising a fluorescence-developing agent and a molecular species bearing a reactive moiety capable of nitrosylation, and optionally containing a saturated solution of copper (I) chloride. Preferably, the kit contains 4,5-diaminofluoroscein (DAF-2). Also, preferably, the reactive moiety capable of transnitrosylation is cysteine.

Preferably, the kit provides the capability of detecting the nitrosylated proteins and identifying the nitrosylated proteins in a sample. Also, preferably, the kit provides the capability of quantifying the amount of nitrosylated species in a biological sample using the kit.

DETAILED DESCRIPTION OF THE INVENTION

Figure 1:
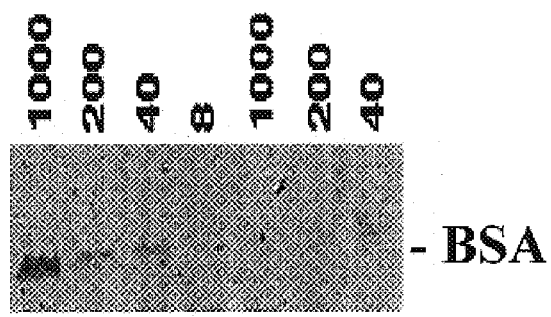
FIG. 1 shows the fluorescence from 8 nM to 1000 nM of S-nitrosoalbumin (SNOBSA) compared to that of the same concentration of native albumin.
Figure 2:
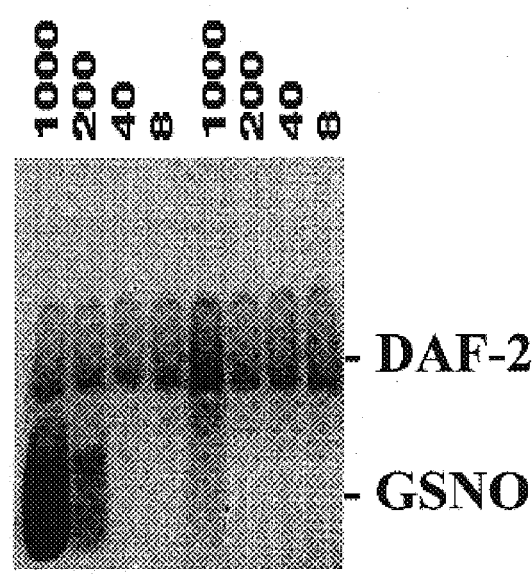
FIG. 2 shows the fluorescence from 8 nM to 1000 nM of S-nitrosoglutathione (GSNO) compared with that of the same concentration of glutathione.

As used herein, "nitrosoprotein" and similar terms encompass any protein that has an —NO group linked through a thiol group, oxygen, carbon, or nitrogen group. S-nitrosoproteins, S-nitrosothiols, and protein S-nitrosylation reactions are terms that refer to compounds with linkage through the thiol (—SH) group. These types of compounds play important roles in cell signaling processes such as neurotransmission, anion channel regulation, host defense and gene regulation.

Although a burgeoning number of articles describe a role for S-nitrosoproteins and protein S-nitrosylation reactions in cell signaling processes such as neurotransmission, anion channel regulation, host defense and gene regulation, the detection of nitrosoproteins has been met with limited success. An important implication is in the FAS induced denitrosylation of Capase-3, which allows lymphocyte apoptosis to proceed. (See Mannick JB, et al. Fas-induced capsase denitrosylation. *Science* 1999, 284: 65.) A method for determining alterations in S-nitrosoprotein concentration following cell signaling events such as the FAS-ligand binding would provide a mechanism for monitoring the progression of apoptosis. The present invention addresses a need for a method for identifying and quantifying levels of S-nitrosoproteins, and other NO equivalents, that would be useful in monitoring the levels of NO in normal and in disease states, for facilitating diagnoses, and in developing more selective drugs for the treatment of such disease states.

The present invention, in one embodiment, is directed towards an improved, practical electrophoresis-based separation and identification method for cellular S-nitrosoproteins that allows for the identification of S-nitrosoproteins in general, in addition to the quantification of alterations in S-nitrosoprotein concentration following cell signaling events. The preferable method of detection produces a signal that is directly proportional to the concentration of the S-nitrosoprotein.

Isolated S-nitrosoproteins (in the absence of catabolic enzymes) are generally quite stable. Protein thiol adducts of NO have relatively long half-lives under physiologic conditions as compared to free NO, thus making detection of nitrosothiol adducts possible.

For the present invention, the source for nitrosoprotein mixtures are typically derived from eukaryotic cells. Though S-nitrosoproteins may be present in virtually all cells, the cell extracts can be prepared from a specific cell type or tissue of a mammalian species, such as human neuroblastoma cells. In accordance with a preferred embodiment of the present invention, the complex mixture of proteins is prepared from mammalian cells in the absence of metal chelators.

The present invention is directed to a method of detecting S-nitrosoproteins in a biological sample containing a mixture of proteins based on the transnitrosylation of nitric oxide to a thiol bearing protein or other macromolecule. Fluorescent output from the reaction of 4,5-diaminofluorescein (DAF-2) and nitric oxide is indicative of their presence. By measuring the fluorescence from the reaction, a quantitative measurement of S-nitrosoproteins can also be obtained.

DAF-2 has been previously used only to measure nitric oxide produced by nitric oxide synthase in situ. In accordance with the present invention, DAF-2 is used for an altogether different purpose: that of identifying nitric oxide evolved from endogenous S-nitrosoproteins. The detection method in this invention is based on correlating the concentration of the S-nitrosoproteins to the amount of cumulative light output from the product of nitric oxide and DAF-2 following excitation. The nitric oxide (NO) is likely generated from transnitrosylation of $NO^+$ from the nitrosoproteins to cysteine, followed by homolytic breakdown of S-nitrosocysteine to NO and/or from direct reaction of $NO^+$ with DAF-2.

The use of S-nitrosocysteine-copper NO evolution as a measurement technique for S-nitrosothiols has been recently reported, (see Fang K, et al., *Reductive Assays for S-nitrosothiols: Implications for measurements in biological systems*. Biochem Biophys Res Commun 1998;252:535-540) however, this technique has not previously been used in conjunction with fluorescence detection or with gel electrophoresis. No previous technique has been successful in identifying S-nitrosoproteins by gel electrophoresis. The present invention addresses the need in the art for a practical system of identifying S-nitrosoproteins by gel electrophoresis. Moreover, the present invention offers the additional capabilities of detecting S-nitrosoproteins on membranes following Western blotting, on a PAGE gel, by Western blot using ultraviolet irradiation before or after reaction with DAF-2, and in solution following protein isolation. In the case of solutions, a fluorescence detection system for solutions, as opposed to an inverted microscopy setup, is required.

The method of detecting nitrosoproteins thus comprises the steps of contacting the biological sample of mixed proteins with a developing reagent, exposing the sample to an excitation light source and detecting the emitted fluorescence. In accordance with one embodiment, the developing agent is comprised of 4,5-diaminofluorescein (DAF-2) and L-cysteine (or any other suitable molecule that bears a thiol group capable of a transnitrosylation reaction) in a saturated solution of CuCl. More particularly, the developing reagent comprises 100 mM L-cysteine in a saturated solution of CuCl (pH 6) to which about 2.5 to about 10 µM DAF-2 is added immediately before the developing reagent is placed in contact with the biological sample. Transnitrosylation to cysteine and the reaction with copper augment the sensitivity of S-nitrosoproteins to detection by DAF-2. In this embodiment, the amount of S-nitrosoproteins present in the sample is determined based on the intensity of the detected fluorescence relative to a standard curve generated from known concentrations of S-nitrosoproteins.

Alternatively, the method in the present invention involves incubating the proteins at 37° C. with 10-100 µM DAF-2 in a saturated copper solution containing ascorbate and carboxyPTIO (1-100 nM), or exposed to UV light after incubation with DAF-2. The mixture of proteins can then be separated by native polyacrylamide gel electrophoresis. The gel is then exposed to a fluorescent light source at an excitation wave length of 488 nm and scanned on a fluorimager at an emission wave length of around 530 nm. The scanned gel or nitrocellulose is observed for bands of fluorescence from the reaction of $N_2O_3$ and DAF-2. In this embodiment, the amount of S-nitrosoproteins present in the sample is determined based on the intensity of the detected fluorescence relative to a standard curve generated from known concentrations of S-nitrosoproteins.

The proteins of the biological sample can be separated based on their charge, molecular weight, size, and/or pH using standard techniques known to those skilled in the art, before the biological sample is contacted with the detection reagent. For example, the proteins can be separated using chromatographic techniques (such as HPLC) or by polyacrylamide gel electrophoresis. In one embodiment, the complex mixture of proteins is separated on a native gel, and the proteins are transferred to a nitrocellulose or other synthetic membrane that is capable of binding proteins before the proteins are contacted with the detection reagent. Transferring the proteins to a solid matrix may enhance the signal generated when the separated proteins are subsequently contacted with the developing reagent and exposed to an excitation light source.

The developing reagent of the present invention produces a detectable fluorescent signal in the presence of a nitrosoprotein. The developing reagent can be added directly to the mixture containing the proteins, or the proteins can first be separated based on their physical properties and optionally fractionated before contact with the developing reagent.

When the proteins have been separated by agarose, isoelectric focusing or polyacrylamide gel electrophoresis, the surface of the gel (or the surface of the membrane if the proteins were subsequently transferred from the gel to a solid matrix, such as nitrocellulose) is exposed to a thin layer of developing reagent that includes 100 mM L-cysteine in a saturated solution of CuCl, pH 6. DAF-2 (2.5-10 µM) is then added immediately before contact with the gel. This gel is placed over an emission wavelength filter (at about 515 nm). The gel or nitrocellulose is then exposed to a fluorescent light source (excitation wave length 490 nm) and scanned by a fluorimeter at an emission wave length 515 nM or photographed with a camera.

The scanned gel or nitrocellulose is observed for bands of fluorescence. Additionally or alternatively, the film in a camera is developed to measure cumulative light output from the reaction of NO and DAF-2.

In accordance with one embodiment, the nitrosoproteins identified in the gels (based on the emitted fluorescence) can be further characterized by cutting out or otherwise physically isolating the relevant protein bands. One skilled in the art will appreciate the technique of preparative chromatography and other similar methods that allow for the isolation of individual proteins from a mixture separated by chromatographic techniques. The individual proteins can then be further analyzed by techniques known in the art, such as microsequencing or by addition of monoclonal antibodies.

This invention represents an improvement on several currently available prior art techniques. First, in the prior art, DAF-2 has been used only to measure nitric oxide produced by nitric oxide synthase in situ. Here, however, DAF-2 is employed in a new and direct way which allows identification of nitric oxide evolved from endogenous nitrosylated proteins. The reaction with copper in the presence of PTIO increases the sensitivity to detection by DAF-2. The technique of the present invention is thus more sensitive and capable of detecting micromolar concentrations, and much simpler than the prior art techniques.

Figure 3:
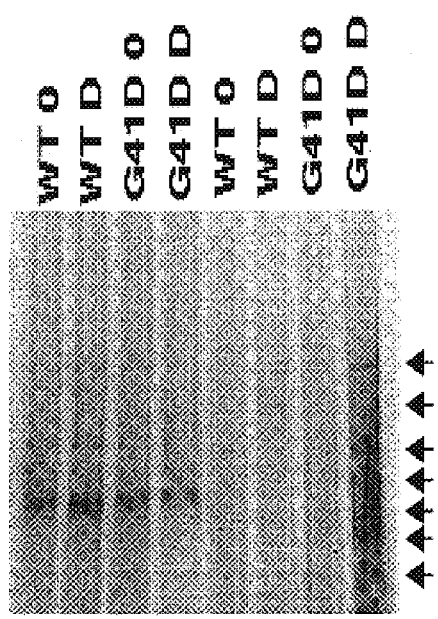
FIG. 3 shows the fluorescence of cytoplasmic (Cyto) and mitochondrial (Mito) proteins obtained from undifferentiated (O) or differentiated (D) neuroblastoma cells expressing wild-type (WT) or mutant (G41D) superoxide dismutase. The arrows indicate proteins with increased fluorescence in the mitochondrial fraction of cells expressing G41D.

Additionally, this invention is capable of the detection of nitrosylated proteins in solution following protein isolation procedures like chromatography. A fluorescence detection system for solutions, as opposed to an inverted microscopy setup (used for analysis of S-nitrosylated proteins on gels) would be required. The invention also allows for the isolation of individual proteins by cutting or otherwise removing fluorescent bands from gels and sequencing and identifying the nitrosylated proteins in cell lysates as shown in FIG. 3. The invention may also be used with 2-dimensional gels for proteomic analysis.

Two specific improvements over the prior art of this technique include the increased sensitivity for identifying very low concentrations of endogenous nitrosylated proteins and improved signal-to-noise ratio on the gels. Increasing the sensitivity and improving the signal-to-noise ratio requires variations in the volumes and concentrations of DAF-2 solution, UV light administration, buffer compositions, and timing of application. For instance, the assay sensitivity will be increased if buffers are developed in which DAF-2 fluorescent intensity is maximized. Additionally, or alternatively, the resolution in measuring nitrosylated proteins from other "background" proteins can achieved by varying gel compositions, thickness, electrophoresis voltages, and buffers. For instance, the stability of S-nitrosoproteins is enhanced when run on isoelectric focusing gels as opposed to polyacrylamide gels. Finally, it is anticipated that additional known fluorescent probes such as dihydrorhodamine-derivatives can be used in the context of the present invention to increase the specificity and sensitivity of the claimed method.

EXAMPLE 1

Various concentrations of S-nitrosylated albumin or unmodified albumin were incubated with 3 µM DAF-2 for 15 minutes at 37° C. An equal volume of 100 µM CuCl, 1 µM ascorbate and 100 nM PTIO was then added to each sample and the sample was incubated for another 15 minutes at 37° C. The samples were then loaded onto a 12% nondenaturing, nonreducing gel and run for 30 minutes at 30 volts. The gel was placed on a Molecular Dynamics STORM 860 fluorescent Scanner and exposed to an excitation wavelength of 480 nM. The scanner detects all emissions greater than 520 nM. The scanned gel in the figure had been incubated in the presence of CuCl/cys for 1 hour and 20 minutes at the time of scanning.

FIG. 1 shows fluorescence from 100 µm S-nitrosoalbumin (Lanes 1 and 2) compared with that of the same concentration of native albumin (Lane 3). Of note, native albumin is endogenously S-nitrosylated to a limited extent.

What is claimed is:

1. A method for detecting the presence of nitrosylated species in a biological sample comprising one or more amino acid-based species, the method comprising the steps of:
    (a) separating the amino acid-based species in the sample;
    (b) contacting the separated species with developing reagents comprising a fluorescence-developing agent that produces a detectable signal in the presence of nitric oxide;
    (c) contacting the separated species with a molecular species bearing a thiol moiety capable of transnitrosylation and a saturated solution of copper (I) chloride;
    (d) exposing the separated species to excitation radiation; and
    (e) detecting emitted fluorescence from the fluorescence-developing agent, wherein the emitted fluorescence indicates the presence of a nitrosylated species in the sample.

2. The method of claim 1, wherein the nitrosylated species comprises an adduct between NO and an amino acid-based species, and wherein the adduct is formed between NO and an atom on the amino acid-based species selected from the group consisting of sulfur, oxygen, nitrogen and carbon.

3. The method of claim 2, wherein the adduct comprises a nitrosylated protein.

4. The method of claim 1, wherein the fluorescence-developing agent comprises a dihydrorhodamine derivative.

5. The method of claim 1, wherein the fluorescence-developing agent comprises 4,5-diaminofluoroscein (DAF-2).

6. The method of claim 1 wherein the method is further capable of quantitating an amount of nitrosylated species detected in the biological sample.

7. The method of claim 1, wherein the method comprises the additional step of incubating the separated species to which has been added the fluorescence-developing agent at an elevated temperature, in the presence of ascorbate and 2-(4-carboxyphenyl)-4,4,5,5-tetramethylimidazolin-1-oxyl 3-oxide (carboxyPTIO).

8. The method of claim 1, wherein the biological sample is derived from mammalian cells in the absence of metal chelators.

9. The method of claim 1, wherein the method comprises the additional step of transferring the separated species to a solid support material capable of binding the species, prior to contacting the species with the developing reagents.

10. The method of claim 1, wherein the separation is achieved by a method selected from the group consisting of agarose gel electrophoresis, polyacrylamide gel electrophoresis, isoelectric focusing, High Performance Liquid Chromatography (HPLC), and preparative chromatography.

11. The method of claim 1, wherein the method comprises the additional step of determining the chemical identity of one or more individual nitrosylated species from the biological sample.

12. A method for detecting the presence of nitrosylated species in a biological sample comprising one or more amino acid-based species, the method comprising the steps of:
(a) separating the amino acid-based species in the sample;
(b) contacting the separated species with developing reagents comprising a fluorescence-developing agent that produces a detectable signal in the presence of nitric oxide;
(c) administering UV light to the separated species;
(d) exposing the separated species to excitation radiation; and
(e) detecting emitted fluorescence from the fluorescence-developing agent,
wherein the emitted fluorescence indicates the presence of nitrosylated species in the sample.

13. The method of claim 12, wherein the nitrosylated species comprises an adduct between NO and an amino acid-based species, and wherein the adduct forms between NO and an atom on the amino acid-based species selected from the group consisting of sulfur, oxygen, nitrogen and carbon.

14. The method of claim 13, wherein the adduct comprises a nitrosylated protein.

15. The method of claim 12 wherein the method is further capable of quantifying an amount of nitrosylated species detected in the biological sample.

16. The method of claim 12, wherein the biological sample comprises a mixture of proteins derived from eukaryotic cells.

17. The method of claim 12, wherein the method comprises the additional step of transferring the separated species to a solid support material capable of binding the species, prior to contacting the species with the developing reagents.

18. The method of claim 12, wherein the separation is achieved by a method selected from the group consisting of agarose gel electrophoresis, polyacrylamide gel electrophoresis, isoelectric focusing, High Performance Liquid Chromatography (HPLC), and preparative chromatography.

19. The method of claim 12, wherein the method comprises the additional step of determining the chemical identity of one or more individual nitrosylated species from the biological sample.

20. The method of claim 12, wherein the fluorescence-developing agent comprises 4,5-diaminofluoroscein (DAF-2).

21. The method of claim 12, wherein the fluorescence-developing agent comprises a dihydrorhodamine derivative.

22. A kit for detecting nitrosylated species in a biological sample, the kit comprising a fluorescence-developing agent that produces a detectable signal in the presence of nitric oxide, a molecular species bearing a thiol moiety capable of nitrosylation, and a saturated solution of copper (I) chloride.

23. A method for identifying nitrosylated species in a biological sample using the kit of claim 22.

24. A method for quantifying the amount of nitrosylated species in a biological sample using the kit of claim 22.

25. The kit of claim 22, wherein the fluorescence-developing agent comprises a dihydrorhodamine derivative.

26. The kit of claim 22, wherein the fluorescence-developing agent comprises 4,5-diaminofluoroscein (DAF-2).

* * * * *